United States Patent
Laudano et al.

(10) Patent No.: US 6,943,361 B2
(45) Date of Patent: Sep. 13, 2005

(54) TANNING LAMP HAVING GROOVED PERIPHERY

(75) Inventors: Joseph D. Laudano, West Haven, CT (US); Prasad S. Sastry, Milford, CT (US); Albert Louis Winkler, Woodbury, CT (US); Michael G. Manning, Milford, CT (US)

(73) Assignee: Voltarc Technologies Inc., Waterbury, CT (US)

( * ) Notice: Subject to any disclaimer, the term of this patent is extended or adjusted under 35 U.S.C. 154(b) by 106 days.

(21) Appl. No.: 10/146,771

(22) Filed: May 16, 2002

(65) Prior Publication Data

US 2003/0155536 A1 Aug. 21, 2003

(Under 37 CFR 1.47)

Related U.S. Application Data

(63) Continuation-in-part of application No. 10/077,279, filed on Feb. 15, 2002.

(51) Int. Cl.[7] .............................................. H01J 61/33
(52) U.S. Cl. .................................. 250/504 R; 313/493
(58) Field of Search ........................... 250/504 R, 356, 250/461.2; 313/485, 493

(56) References Cited

U.S. PATENT DOCUMENTS

| | | | |
|---|---|---|---|
| 2,916,645 A | 12/1959 | Lemmers et al. | |
| 2,924,732 A | 2/1960 | Lehmann | |
| 3,129,085 A | 4/1964 | Olsen et al. | |
| D198,268 S | 5/1964 | Thorington et al. | |
| 3,169,657 A | 2/1965 | Olsen | |
| 3,225,241 A | 12/1965 | Spencer et al. | |
| 3,466,443 A | 9/1969 | Roesler et al. | |
| 3,560,786 A | * 2/1971 | Shurgan | 313/493 |
| 3,676,728 A | 7/1972 | Schreurs | |
| 3,717,781 A | 2/1973 | Sadoski et al. | |
| 3,767,956 A | 10/1973 | Bauer | |
| 3,988,633 A | 10/1976 | Shurgan et al. | |
| 4,001,628 A | 1/1977 | Ryan | |
| 4,103,175 A | 7/1978 | Levin | |
| 4,389,295 A | 6/1983 | Davey et al. | |
| 4,434,385 A | 2/1984 | Touho et al. | |
| 4,499,403 A | 2/1985 | Leppelmeier et al. | |
| 4,591,958 A | 5/1986 | Lamboo | |
| 4,645,969 A | 2/1987 | Hoffman | |
| 4,703,224 A | 10/1987 | Rattray et al. | |
| 4,791,336 A | 12/1988 | Morimoto et al. | |
| 4,825,125 A | 4/1989 | Lagushenko et al. | |
| 4,933,600 A | 6/1990 | Endres | |
| 4,959,551 A | 9/1990 | Schlitt | |
| 5,216,323 A | 6/1993 | Baaten et al. | |
| 5,223,341 A | 6/1993 | Sigai | |
| 5,539,277 A | 7/1996 | Jansma | |
| 5,557,112 A | * 9/1996 | Csoknyai et al. | 250/504 R |
| 5,565,685 A | 10/1996 | Czaka et al. | |
| 6,494,901 B1 | * 12/2002 | Doty | 607/91 |

FOREIGN PATENT DOCUMENTS

EP        0 228 737 A3      7/1987

* cited by examiner

Primary Examiner—John R. Lee
Assistant Examiner—James J. Leybourne
(74) Attorney, Agent, or Firm—David J. Silvia; Edwards & Angell, LLP

(57) ABSTRACT

The present disclosure provides a device and method for exposing a person to ultraviolet radiation in tanning wavelengths which is emitted from a discharge lamp having a plurality of grooves formed in its outer periphery along a helical path. The discharge lamp includes, inter alia, an elongated vitreous tube, first and second electrode assemblies and a coating on the interior the interior of the tube. The coating is applied on an interior of the tube along the entire length for emitting ultraviolet radiation in tanning wavelengths when a voltage is applied across the first and second electrodes. In a first representative embodiment, the plurality of grooves are interconnected and the helical path is continuous. Alternatively, the plurality of grooves can be axially offset and the helical path can be discontinuous.

23 Claims, 6 Drawing Sheets

TANNING LAMP HAVING GROOVED PERIPHERY

CROSS-REFERENCE TO RELATED APPLICATIONS

The subject application is a continuation-in-part of commonly owned U.S. patent application Ser. No. 10/077,279, filed Feb. 15, 2002, which is herein incorporated by reference in its entirety.

BACKGROUND OF THE INVENTION

1. Field of the Invention

The present invention relates generally to discharge lamps, and more particularly, to a discharge lamp for use in tanning applications, wherein the lamp includes a vitreous tube having a series of grooves formed in its periphery.

2. Background of the Related Art

Discharge lamps have been in existence for many decades. Discharge lamps consist primarily of an elongated vitreous tube having axially opposed end seals and coated on the inside with phosphor powders which fluoresce when excited by ultraviolet light. Filament electrodes are mounted on the end seals of the tube and are connected to base pins which engage with the lamp housing. The elongated tube is filled with a rare gas, such as argon, and a drop of mercury.

Discharge lamps typically operate at a relatively low pressure. In operation, an alternating current is applied to the electrodes which increases the electrode temperature and causes the emission of electrons therefrom. These electrons are accelerated by the voltage across the tube until they collide with the mercury atoms, causing them to be ionized and excited. When the mercury atoms return to their normal state, mercury spectral lines in both the visible and ultraviolet region are generated. The ultraviolet radiation excites the phosphor coating to luminance. The resulting output is not only much higher than that obtained from the mercury lines alone, but also results in a continuous spectrum with colors dependent upon the phosphors used.

Typically, the intensity of the ultraviolet radiation emitted from the discharge lamp differs along the length of the lamp, but does not vary dramatically nor are distinct regions of varying intensity created. In applications such as tanning, which will be discussed in more detail supra, it would be advantageous to have distinct regions of ultraviolet radiation intensity.

Since the late 1970s, the practice of tanning, defined as the darkening of one's skin through exposure to ultraviolet (UV) radiation, has increased in popularity in the United States. Each person's skin reacts differently to UV radiation exposure, with the reaction being dependent upon genetically determined factors, such as the amount of melanin pigment already in the skin naturally and the capability of the person's skin to produce additional melanin (facultative pigmentation).

Melanin is the dark pigment found in the retina, hair and skin, except for the palms of the hands, soles of the feet and lips. Without the protection afforded by the melanin pigment, a person's skin would burn when exposed to UV radiation. As stated above, the skin includes naturally occurring melanin pigment and produces additional melanin. Melanin is produced by special cells called melanocytes, which are located deep within the outer layer of the skin. When the melanocytes are stimulated by ultraviolet light, they utilize an amino acid called tyrosine to produce the pigment melanin. Since the melanin pigment is only able to absorb ultraviolet light of approximately 260–320 nanometers, UVB radiation is needed to achieve melanin production. UVA radiation which has a wavelength of approximately 320–400 nanometers can formulate melanin, but only when there is enough photosensitizing material already in the skin to trigger a UVB reaction. With the presence of UVB, melanocytes are stimulated to divide, creating more pigment cells. During this time, the epidermis thickens to form additional protection, a condition referred to as acanthosis.

In the beginning stages of melanin production, the skin has very little melanin or radiation protection capabilities. As a result, UVA radiation is not blocked by melanin pigments and, due to its longer wavelength, penetrates the skin deeper than UVB, causing damage to the corium. Damage to this layer of the epidermis hastens aging and destruction of collagen and connective tissue. A UVA burn can be much more damaging because it is not felt due to its deep penetration.

In order for the pigmentation process to be effective, melanin granules must be oxidized or darkened, which requires a high dose of long-wave UVA. Consequently, exposure to UVB radiation functions to create melanin pigment, while UVA exposure ensures the oxidation of the pigment. Together, a the proper combination of UV exposure operates to create a light-protection mechanism.

It is well recognized that to obtain the desired uniform tan, a person's facial region often requires the application of more intense radiation than the body region. This is due to the higher levels of melanin pigment present in the face, resulting from a more frequent exposure to the sun than the body. Prior attempts at designing a tanning chamber which provides a more uniform tan have included a lamp assembly which utilizes separate and distinct bulbs in the facial region. More specifically, higher intensity metal halide bulbs are positioned in the facial region and lower intensity bulbs extend over the body.

U.S. Pat. No. 5,557,112 to Csoknyai et al. discloses a fluorescent lamp having distinct and adjacent first and second zones along its length with different ultraviolet radiation characteristics. The first zone of the lamp has a first fluorescent coating applied to the inner surface of the tube for producing ultraviolet radiation having desired radiation characteristics. The second zone of the lamp has a second fluorescent coating applied to the tube for producing ultraviolet radiation having radiation characteristics which are different from those produced in the first zone.

Although these prior attempts may contribute to a more uniform tanning effect, they are more complicated to fabricate and maintain and are relatively expensive. This is especially true when the lamp is used in an application that requires more than two regions of varying intensity.

The patent literature also includes disclosures concerning tubular lamp assemblies that include constricted portions or grooves. See e.g., U.S. Pat. No. 2,916,645 to Lemmers et al.; U.S. Pat. No. 3,129,085 to Olsen et al.; U.S. Pat. No. 4,825,125 to Lagushenko et al; U.S. Pat. No. 3,988,633 to Shugan et al.; and Des. 198,268. The prior art patent disclosures also teach conventional systems and processes for forming such constricted portions and/or grooves in tubular lamps.

There is a continuing need for discharge lamps for use in applications such as tanning that provide enhanced lamp performance and/or energy delivery.

SUMMARY OF THE INVENTION

The present invention is directed to and provides a discharge lamp which includes, inter alia, an elongated vitreous tube, first and second electrode assemblies and a coating on the interior the interior of the tube. The elongated vitreous tube has an outer periphery and axially opposed first and second ends which define an axial length for the tube therebetween. Preferably, the length of the vitreous tube is approximately 72 inches.

The outer periphery has a plurality of grooves defined therein and positioned along an axially extending helical path. Additionally, the first electrode assembly is associated with the first end of the tube and the second electrode assembly is associated with the second end of the tube. A coating is applied on an interior of the tube along the entire length for emitting ultraviolet radiation in tanning wavelengths when a voltage is applied across the first and second electrodes.

In a first representative embodiment, the plurality of grooves are interconnected and the helical path is continuous. Alternatively, the plurality of grooves can be axially offset and the helical path can be discontinuous.

Preferably, the grooves are formed in the outer periphery of the tube so as to have a pitch of between about 2 inch and about 12 inch and a depth of between about 0.100 inch to about 0.250 inch. As used herein, groove pitch is defined as the distance from a point on a groove to a corresponding point on the next or adjacent groove measure parallel to the axis and is synonymous with the axial spacing. Additionally, it is envisioned that the grooves are formed in the outer periphery so as to have a ratio of the groove pitch to the groove depth of about between 8 (in/in) to about 120 (in/in).

It is envisioned that the grooves are formed in the outer periphery so as to have a width of about 0.250 inch to 1.0 inch and a ratio of the groove pitch to the groove width of about between 2 (in/in) to about 48 (in/in). Additionally, it is presently envisioned, but not required, that the depth of each groove does not exceed 10 percent of the outside diameter of the tube.

It is also envisioned that the discharge lamp of the present disclosure further includes a reflective coating on the interior of the vitreous tube and which is positioned radially inward of the coating. The reflective coating extends about a portion of the vitreous tube circumference.

The present disclosure is also directed to a device for effectuating tanning of a person's skin. The tanning device includes, inter alia, a housing structure and a discharge lamp assembly. The housing structure has a body portion and a base portion. The body portion defines an internal tanning chamber which is adapted and configured for receiving the person.

The discharge lamp assembly is disposed within the internal tanning chamber and includes an elongated vitreous tube, first and second electrode assemblies and a coating on the interior the interior of the tube. The elongated vitreous tube has an outer periphery and axially opposed first and second ends which define an axial length for the tube therebetween. Preferably, the length of the vitreous tube is approximately 72 inches. The outer periphery has a plurality of grooves defined therein and positioned along an axially extending helical path.

The first electrode assembly is associated with the first end of the tube and the second electrode assembly is associated with the second end of the tube. A coating is applied on an interior of the tube along the entire length for emitting ultraviolet radiation in tanning wavelengths when a voltage is applied across the first and second electrodes.

The present disclosure is also directed to a method of exposing a person to ultraviolet radiation. The method includes the steps of positioning a discharge lamp assembly in proximity to a person and energizing said discharge lamp for a period of time to effect skin tanning of said person.

The discharge lamp includes an elongated vitreous tube having an outer periphery and axially opposed first and second ends which define an axial length for the tube therebetween. The outer periphery has a plurality of grooves defined therein and formed along a helical path. The lamp further includes a first electrode assembly which is associated with the first end of the tube and a second electrode assembly which is associated with the second end of the tube. A coating is applied to the interior of the vitreous tube along the entire length for emitting ultraviolet radiation in tanning wavelengths when a voltage is applied across the first and second electrodes.

BRIEF DESCRIPTION OF THE DRAWINGS

So that those of ordinary skill in the art to which the subject invention pertains will more readily understand how to make and use the system and method described herein, preferred embodiments will be described in with reference to the drawings, wherein:

FIG. 3b is a cross-sectional view of the discharge lamp of FIG. 3a taken along line 3b—3b and illustrating an internal reflector coating disposed within the lamp core which defines an aperture window;

FIG. 3c illustrates an exploded cross-sectional view of the area identified as 3c in FIG. 3a;

DESCRIPTION OF PREFERRED EMBODIMENTS

Reference is now made to the accompanying figures for the purpose of describing, in detail, preferred embodiments of the present disclosure. The figures and accompanying detailed description are provided as examples of the disclosed subject matter and are not intended to limit the scope thereof.

Figure 1:
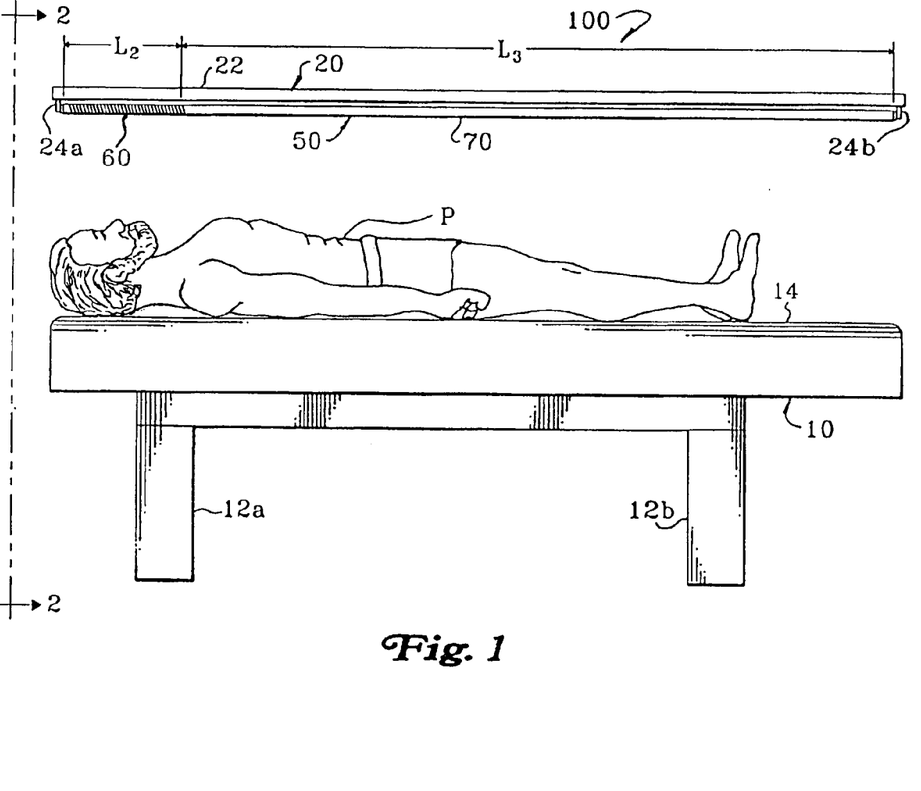
FIG. 1 is an elevational view of a tanning chamber which includes a plurality of discharge lamps that are constructed in accordance with an embodiment of the present disclosure.
Figure 2:
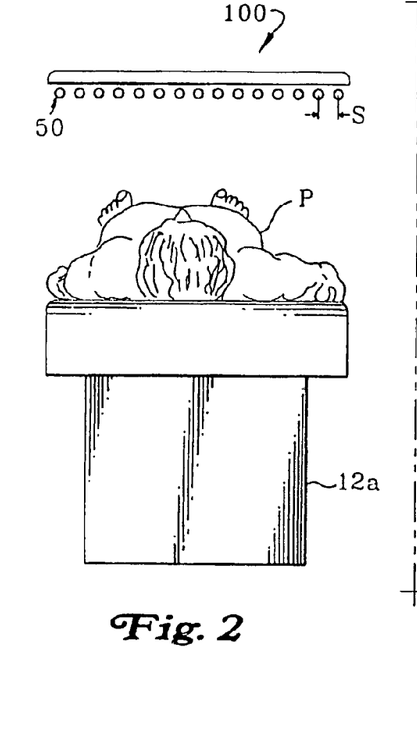
FIG. 2 illustrates a sectional view of the tanning chamber of FIG. 1 taken along line 2—2.

Referring now to FIGS. 1 and 2, there is illustrated a tanning chamber constructed in accordance with a preferred embodiment of the present disclosure and designated generally as reference numeral 100. Tanning chamber 100 primarily includes tanning bed 10 and lamp assembly 20. Tanning bed 10 is supported by leg members 12a and 12b and is generally configured so that surface 14 is parallel with the floor (not shown) and lamp assembly 20. However, those skilled in the art would readily appreciate that tanning chamber 100 can be configured as a vertically oriented tanning booth without departing from the inventive aspects disclosed herein.

Lamp assembly 20 includes housing 22, electric contacts 24a and 24b, and fifteen (15) discharge lamps 50. Discharge lamps 50 are electrically engaged with contacts 24a and 24b and are adapted and configured so as to emit ultraviolet light in the substantially downward direction when an alternating current is applied thereto. Lamps 50 will be discussed in greater detail supra. Those skilled in the art would readily appreciate that the quantity and spacing "s" of discharge lamps 50 can be selectively adjusted based on factors such as, but not limited to, the width of tanning chamber 100, the distance between lamp assembly 20 and surface 14, the outside diameter of lamps 50, and the desired radiation intensity.

A person "P" is positioned on surface 14 of tanning bed 10 such that the frontal region of person P faces lamp assembly 20. As a result, the frontal region of person P is exposed to the ultraviolet light emitted from lamp assembly 20 and is tanned thereby. As shown in FIG. 1, discharge lamp 50 includes a first region 60 and second region 70 axially deployed or arranged along length $L_1$ (see FIG. 3a) of lamp 50. The lengths of the first and second regions 60 and 70, are identified as $L_2$ and $L_3$ respectively. The first region 60 is advantageously configured and dimensioned to be positioned over the facial portion of person P and the second region 70 is generally configured and dimensioned to extend over the body portion. In an exemplary embodiment of lamp assembly 20, the length of the facial region, and thus $L_2$, is approximately 18 inches.

Figure 3A:
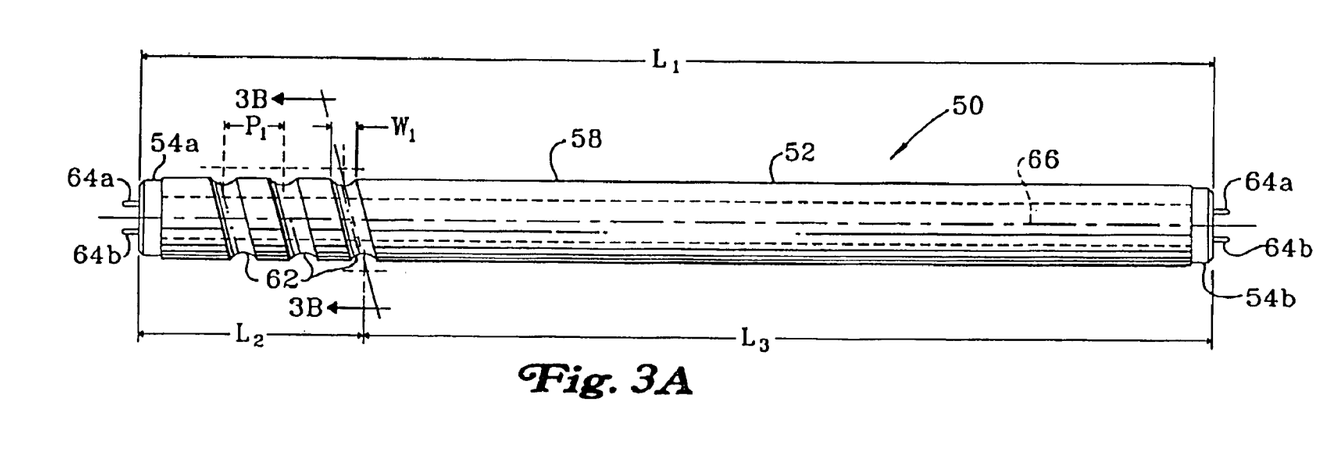
FIG. 3a illustrates a discharge lamp constructed in accordance with an embodiment of the present disclosure having a series of axially spaced grooves formed in a portion of the periphery of the tube.
Figures 3B, 3C:
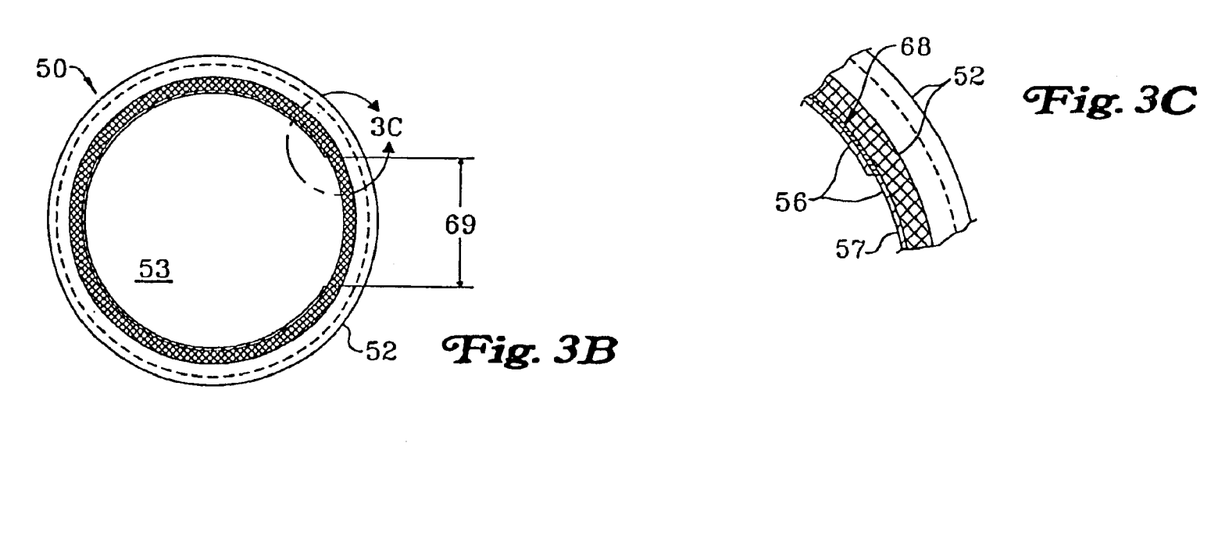

Referring now to FIGS. 3a–3c, there is illustrated lamp 50 which includes an elongated vitreous tube 52, first and second end seals 54a and 54b, and first and second electrodes (not shown). Tube 52 has a phosphor coating 56 applied to interior surface 57 and has a drop of mercury disposed within central core 53. Tube 52 has an outer periphery 58 which extends axially between the first and second end seals 54a and 54b. The overall length of tube 52 is identified as $L_1$. Typically in a tanning application, such as illustrated herein, the overall length of tube 52 is approximately 72 inches or 6 feet. As would be readily appreciated by those skilled in the art to which the present disclosure appertains, the length of each region and the overall length of the tube can be selectively adjusted based on the intended application.

The first electrode assembly is associated with the first end seal 54a and the second electrode assembly is associated with the second end seal 54b. Each electrode assembly includes pins 64a and 64b which electrically communicate with corresponding electrical contacts 24a and 24b associated with lamp assembly 20. In an alternate embodiment, pins 64a and 64b can be replaced with a recessed double contact base or any other suitable electrical communication means, as would be readily appreciated by those skilled in the art.

In operation, an alternating current is applied to the pins 64a and 64b which increases the temperature of the electrodes and causes the emission of electrons therefrom. These electrons are accelerated by the voltage across the tube 52 until they collide with the mercury atoms, causing them to be ionized and excited. When the mercury atoms return to their normal state, mercury spectral lines in both the visible and ultraviolet region are generated. The ultraviolet radiation excites the phosphor coating 56 to luminance and generates a higher intensity UV output.

As stated above, the outer periphery 58 of tube 52 includes first region 60 and second region 70 having lengths $L_2$ and $L_3$, respectively. The first region 60 has a continuous helical groove path that defines a series of axially spaced apart grooves 62 formed therein, each having a width of $W_1$. It should be noted that although in the embodiment shown herein, the groove path is continuous, it is envisioned that the groove path can be discontinuous. Grooves 62 have an axial spacing $P_1$ and are formed in a plane which intersects axis 66 at an acute angle. Due to the presence of grooves 62, a portion of the arc stream which extends between the axially opposed electrodes tends to travel in a generally sinusoidal path in first region 60. As a result, the arc stream length in this region is increased without increasing the length $L_2$ of first region 60. In addition, due to the restriction caused by grooves 62, in this region, the arc stream travels closer to the periphery 58 of tube 52. Each of the foregoing physical properties and conditions advantageously serves to improve the recombination rate of the mercury ions with the phosphor coating 56. Consequently, the intensity of the ultraviolet radiation in first region 60 is increased and is therefore higher than the UV intensity in second region 70 (all other variables being equal).

An exemplary embodiment of tube 52 further includes reflective coating 68 which is adapted and configured to direct the ultraviolet radiation in the substantially downward direction, e.g., through aperture 69. Reflective coating 68 is positioned adjacent to interior surface 57 and is radially outward of phosphor coating 56 and extends over a portion of the circumference of interior surface 57. Preferably reflective coating 68 extends over approximately 300 degrees of the circumference. In the embodiment shown in FIG. 3a, reflective coating 68 extends axially over length $L_2$. In addition to directing the ultraviolet radiation in a substantially downward direction, reflective coating 68 aids in focusing the UV radiation generated in first region 60 over the facial region. More particularly, the reflective coating 68 generally reduces the amount of refraction which normally occurs due to the vitreous tube 52 and causes the radiant energy to be axially dispersed.

It should be noted that the shape (e.g., width), size (e.g., depth), spacing and orientation (e.g., angle) of the grooves can be selectively adjusted in order to achieve a desired intensity within a region. For example, by increasing the depth of grooves 62, thereby bringing the arc stream closer to periphery 58, the intensity in first region 60 is further increased. Also, by orienting the grooves 62 at an angle with respect to axis 66, a larger portion of periphery 58 is deformed than is deformed when the grooves are formed in a plane perpendicular to axis 66. Additionally, when the grooves 62 are angled, the cross-section of periphery 58 is non-circular in the groove locations. The presence of a larger amount of deformed surface area and the non-circular cross-section each further increases the arc stream length and the plasma recombination efficiency adjacent to the phosphor.

As clearly illustrated above, the formation of grooves 62 in first region 60 of tube 52 enables discharge lamp 50 to provide two distinct and predetermined regions of UV intensity. Additionally, through the adjustment of parameters such as the groove depth, spacing, orientation and width, the intensity of the UV radiation emitted from the first region 60 can be selectively established and/or controlled, both from an absolute sense and on a relative basis as compared to an adjacent region that is devoid of such grooves. More specifically, by adjusting any one or a combination of the above-identified parameters, the desired UV output of first region 60 of lamp 50 can be achieved. It should also be noted that, although the first region 60 is shown in FIG. 3a to be positioned adjacent to first end seal 54a, which is preferable for a tanning application, this region can be positioned anywhere along the length of tube 52. In some applications, for example, it may be desired to have a region of higher intensity located at the center of the tube 52.

Figure 4A:
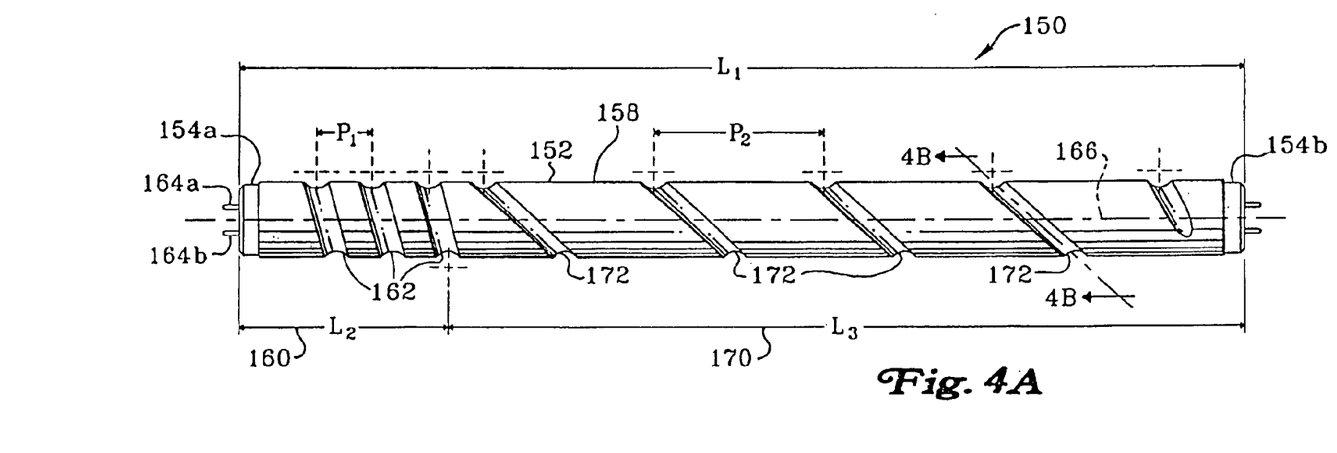
FIG. 4a is an elevational view of a discharge lamp constructed in accordance with an embodiment of the present disclosure having two regions of axially spaced apart grooves formed in the periphery of the vitreous tube.
Figure 4B:
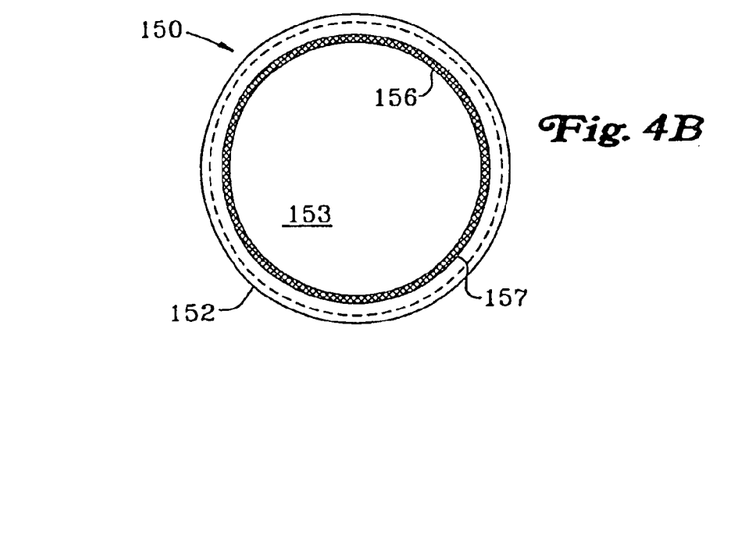
FIG. 4b is a cross-sectional view of the discharge lamp of FIG. 4a taken along line 4b—4b and illustrating the internal fluorescent coating.

Referring now to FIGS. 4a and 4b, there is illustrated an alternate embodiment of the subject discharge lamp designated generally as reference numeral 150. Structural elements of the embodiment shown herein which are similar to those disclosed with respect to the exemplary embodiment of FIGS. 3a–3c are identified by similar reference numerals. As before, discharge lamp 150 includes an elongated vitreous tube 152, first and second end seals 154a and 154b, and first and second electrodes (not shown). Tube 152 has a phosphor coating 156 applied to interior surface 157 and has a drop of mercury disposed within central core 153. Tube 152 has an outer periphery 158 which extends axially between the first and second end seals 154a and 154b. The overall length of tube 152 is identified as $L_1$.

Tube 152 also includes a first region 160 and second region 170, each extending axially along length $L_1$ of lamp 150. The lengths of the first and second regions 160 and 170 are identified as $L_2$ and $L_3$ respectively. However, unlike second region 70 of discharge lamp 50, second region 170 of lamp 150 includes axially spaced apart grooves 172. Grooves 172 have an axial spacing $P_2$ and are oriented at an acute angle with respect to axis 166. The spacing $P_2$ and orientation of grooves 172 are different than the spacing $P_1$ and the orientation of grooves 162 within first region 160. As a result, the UV intensity within second region 170 is different than that emitted from first region 160. It should be noted that FIG. 4a illustrates how two regions of varying intensity can be defined by varying the groove spacing and angular orientation. It should be further noted that the two distinct regions could be defined by varying the groove depth, spacing, orientation and width or combinations thereof. Also, in the embodiment shown in FIG. 4a, the groove spacing and orientation of first region 160 is such that higher intensity UV emission will be present in this region. Alternatively, the groove parameters can be adjusted such that second region 170 has a higher intensity emission if desired for a specific application. Although in the embodiment shown herein, the groove path is continuous, it is envisioned that the groove path can be discontinuous.

Figures 5A, 5B:
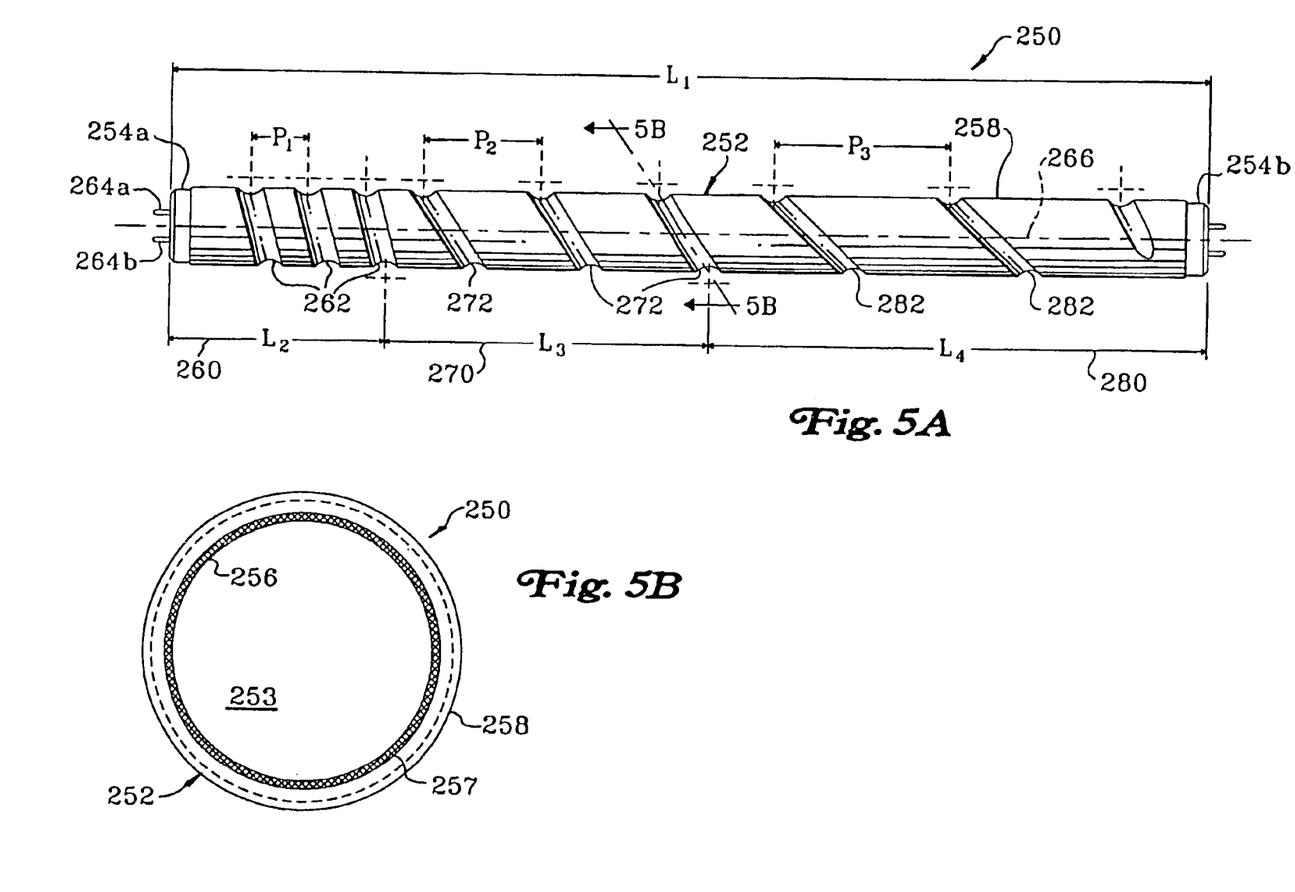
FIG. 5a is an elevational view of a discharge lamp constructed in accordance with an embodiment of the present disclosure having three distinct regions of axially spaced apart grooves formed in the periphery of the vitreous tube.
FIG. 5b is a cross-sectional view of the discharge lamp of FIG. 5a taken along line 5b—5b.

Referring now to FIGS. 5a and 5b, there is illustrated yet another exemplary embodiment of a discharge lamp according to the present disclosure, designated generally as reference numeral 250. Structural elements of the embodiment shown herein which are similar to those disclosed with respect to the exemplary embodiment of FIGS. 3a–3c are identified by similar reference numerals. As before, discharge lamp 250 includes an elongated vitreous tube 252, first and second end seals 254a and 254b, and first and second electrodes (not shown). Tube 252 has a phosphor coating 256 applied to interior surface 257 and has a drop of mercury disposed within central core 253. Tube 252 has an outer periphery 258 which extends axially between the first and second end seals 254a and 254b. The overall length of tube 252 is identified as $L_1$.

Unlike tube 52 of lamp 50, tube 252 includes a first region 260, a second region 270, and a third region 280, each axially arranged or deployed along length $L_1$ of lamp 250. The lengths of the first, second and third regions 260, 270 and 280 are identified as $L_2$, $L_3$ and $L_4$, respectively. In the embodiment disclosed herein, second region 270 and third region 280 of lamp 250 include axially spaced apart grooves 272 and 282, respectively. Grooves 272 and 282 have an axial spacing of $P_2$ and $P_3$ respectively and are both oriented at an acute angle with respect to axis 266. However, the angular orientation of grooves 272 is greater than that of grooves 282. Since the spacing and orientation of the grooves within the first, second and third regions differ, the UV intensity emitted from these regions differ. It should be noted that FIG. 5a illustrates how three regions of varying intensity can be defined by varying the groove spacing and angular orientation. As stated before, the distinct regions can be defined by varying the groove depth, spacing, orientation and width or combinations thereof. It should be noted that although in the embodiment shown herein, the groove path is continuous, it is envisioned that the groove path can be discontinuous.

Figure 6A:
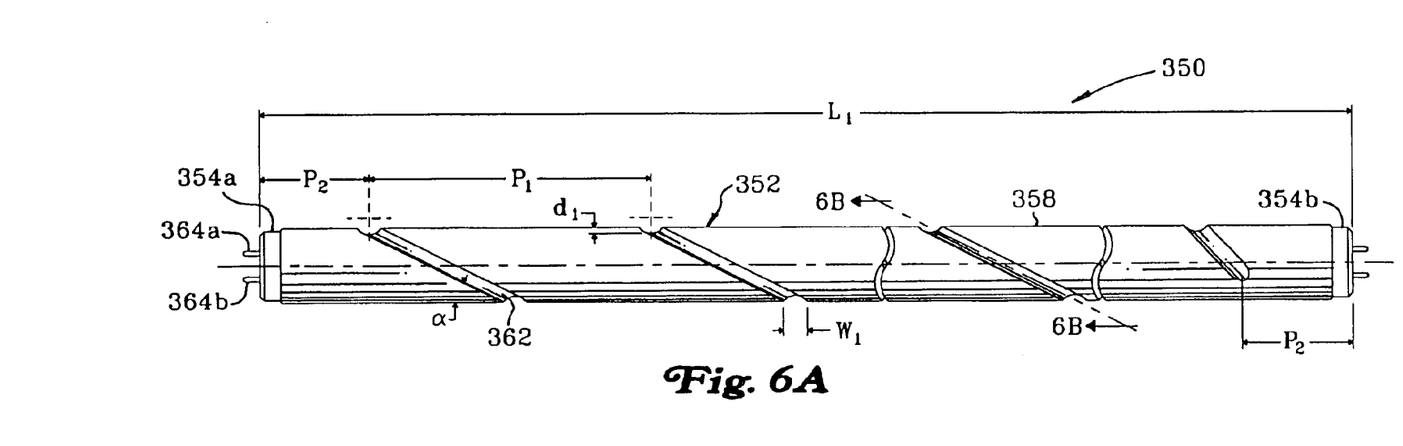
FIG. 6a illustrates a discharge lamp constructed in accordance with an embodiment of the present disclosure having a helical groove path formed in the periphery of the tube.
Figure 6B:
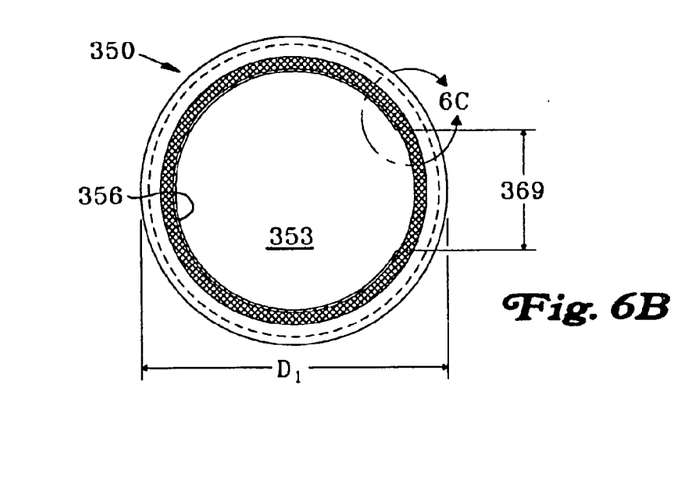
FIG. 6b is a cross-sectional view of the discharge lamp of FIG. 6a taken along line 6b—6b and illustrating an internal reflector coating disposed within the lamp core.
Figure 6C:
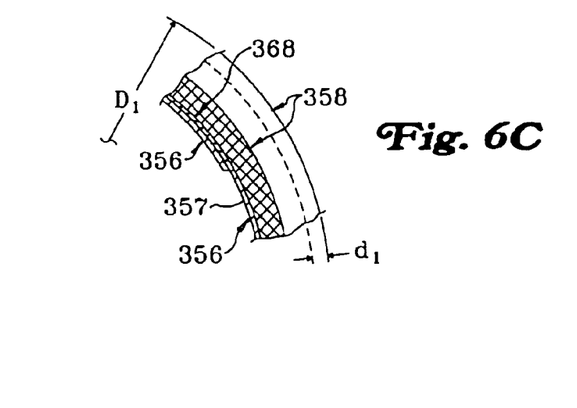
FIG. 6c is an exploded cross-sectional view of the area identified as 6c in FIG. 6a which illustrates an exemplary groove depth according to the present disclosure.

Referring now to FIGS. 6a–6c, there is illustrated a further exemplary lamp 350 according to the present disclosure which is structurally similar to lamps 50, 150 & 250 and is adapted and configured for use in tanning chamber 100 of FIG. 1. Similar to the previously described embodiments, lamp 350 includes an elongated vitreous tube 352, first and second end seals 354a and 354b, and first and second electrodes (not shown). Tube 352 has a phosphor coating 356 applied to interior surface 357 and has a drop of mercury disposed within central core 353. An outer periphery 358 of tube 352 extends axially between the first and second end seals 354a and 354b.

In contrast to the previously described tubes, namely tubes 52, 152 and 252, the outer periphery 358 of tube 352 is not segmented into multiple regions, e.g., first and second regions having lengths $L_2$ and $L_3$, respectively. Outer periphery 358 of tube 352 has a plurality of grooves 362 defined therein which are equally spaced and oriented and positioned along a helical path. The helical path extends axially along substantially the entire length $L_1$ of tube 352, i.e., the helical path extends all the way to, or in close juxtaposition with, end seals 354a, 354b. In the embodiment illustrated in FIG. 6a, the plurality of grooves 362 are interconnected and the helical path is continuous. Alternatively, the grooves 362 can be axially spaced apart and the helical path can be discontinuous.

Each groove 362 has a width of $W_1$, a depth of $d_1$, and an axial spacing or pitch $P_1$. As a result of the being defined along an axially extending helical path, each groove is formed in a plane which intersects axis 366 at an acute angle α. In the representative embodiment shown herein, tube 352 has an outer diameter $D_1$ of 1.5" and the grooves 362 have an axial spacing or pitch $P_1$ of 9.0", a depth $d_1$ of 0.125" and a width $W_1$ of 0.50". Based on the foregoing diameter and pitch, the ratio of pitch over $d_1$ is 72 (in/in). Also, the resulting ratio of the groove pitch to groove width is about 18 (in/in).

As before, due to the presence of grooves 362, a portion of the arc stream which extends between the axially opposed electrodes tends to travel in a generally sinusoidal path along the length of the tube. As a result, the arc stream length in this region is increased without increasing the overall length of the tube. In addition, due to the restriction caused by grooves 362, the arc stream travels closer to the periphery 358 of tube 352. Each of the foregoing physical properties and conditions advantageously serves to provide a lamp which emits ultraviolet radiation having properties and characteristics which are optimal for use in tanning applications. The grooves 362 also function to improve the efficiency of the lamp 350 and result in an operational cost savings when compared to lamps which have an unaltered outer periphery.

The exemplary embodiment of tube 352 further includes reflective coating 368 which is adapted and configured to direct the ultraviolet radiation in the substantially downward direction, e.g., through aperture 369. Reflective coating 368 is positioned adjacent to interior surface 357 and is radially outward of phosphor coating 356 and extends over a portion of the circumference of interior surface 357. It should be noted that although phosphor coating 356 is shown as a single coating layer, phosphor coating 356 can be applied as a multiple coating, a mixture of phosphors or combinations thereof.

Figure 7:
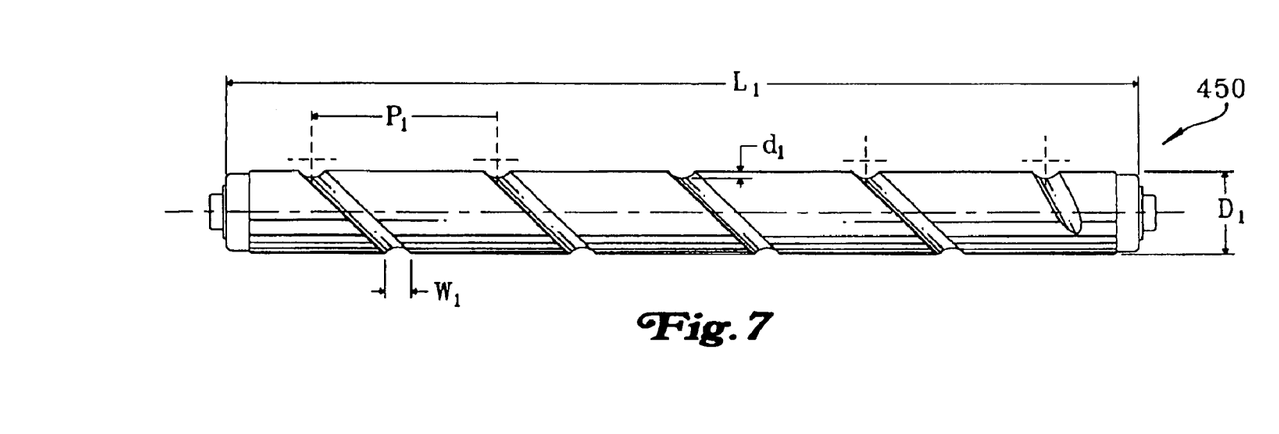
FIG. 7 illustrates a discharge lamp constructed in accordance with an embodiment of the present disclosure wherein axially spaced grooves are formed in the periphery of the tube in a helical pattern.
Figure 8:
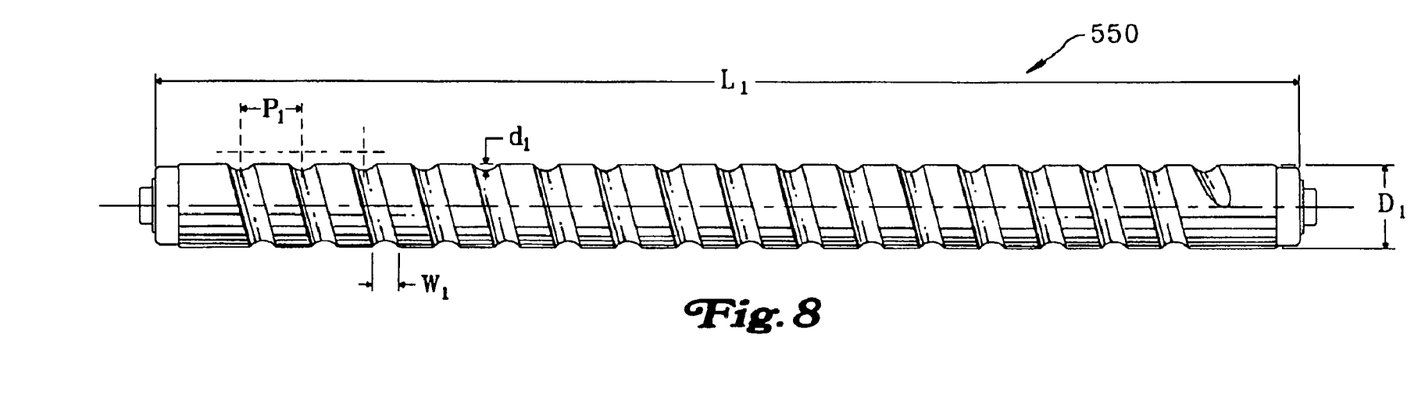
FIG. 8 illustrates a discharge lamp constructed in accordance with an embodiment of the present disclosure wherein the axially spaced grooves formed in the periphery of the tube are relatively tightly spaced.

Referring now to FIGS. 7 and 8 there is illustrated two alternate embodiments of the present discharge lamp which are designated by reference numerals 450 and 550 respectively. Similar to lamp 350, lamps 450 and 550 have an outer periphery which has a plurality of grooves formed therein and positioned along a helical path that extends axially along approximately the entire length $L_1$ of the lamp. However, in contrast to lamp 350, the groove width $W_1$, depth $d_1$, and pitch $P_1$ have been modified to provide alternate embodiments of the improved tanning lamp of the present disclosure.

Through experimentation it has been determined that the following characteristics provide optimal overall performance for grooved tanning lamps:

$d_1$ between about 0.100 inch to about 0.250 inch a ratio of groove pitch to groove depth of about between 8 (in/in) to about 120 (in/in)

$W_1$ between about 0.250 inch to 1.0 inch and a ratio of groove pitch to groove width of about between 2 (in/in) to about 48 (in/in)

a groove depth not exceeding 10 percent of the outside diameter of the tube

Lamps configured to have the above identified groove properties, provide a UV radiation source for tanning applications which is aesthetically pleasing, stronger and more efficient than prior art lamps, in addition to satisfying all FDA regulations applied to tanning lamps.

It is not intended that the present disclosure be limited to lamps having the above-identified characteristics. However, lamps having represent characteristics presently preferred, representative configurations and yield advantageous results for tanning applications.

While exemplary discharge lamps have been described with respect to various specific embodiments, those of ordinary skill in the art will readily appreciate that various modifications, changes, and enhancements may be made thereto without departing from the spirit and scope of the invention as defined by the appended claims.

What is claimed is:

1. A discharge lamp for use in tanning applications comprising:

an elongated vitreous tube having an outer periphery and axially opposed first and second ends which define an axial length for the tube therebetween, the outer periphery having a plurality of grooves defined therein and positioned along an axially extending helical path, wherein the plurality of grooves are axially offset and the helical path is discontinuous;

a first electrode assembly associated with the first end of the tube;

a second electrode assembly associated with the second end of the tube; and a coating on an interior of the tube along the entire length for emitting ultraviolet radiation in tanning wavelengths when a voltage is applied across the first and second electrodes.

2. A discharge lamp as recited in claim 1, wherein the grooves are formed in the outer periphery of the tube having a pitch between about 2 inches and about 12 inches.

3. A discharge lamp as recited in claim 2, wherein the grooves formed in the outer periphery have a depth of between about 0.100 inch to about 0.250 inch.

4. A discharge lamp as recited in claim 3, wherein the grooves are formed in the outer periphery so as to have a ratio of the groove pitch to the groove depth of about between 8 (in/in) to about 120 (in/in).

5. A discharge lamp as recited in claim 2, wherein the grooves are formed in the outer periphery so as to have a width of about 0.250 inch to 1.0 inch and a ratio of the groove pitch to the groove width of about between 2 (in/in) to about 48 (in/in).

6. A discharge lamp as recited in claim 1, wherein the depth of each groove does not exceed 10 percent of the outside diameter of the tube.

7. A discharge lamp as recited in claim 1, further comprising a reflective coating on the interior of the vitreous tube and positioned radially inward of the coating, the reflective coating extending about a portion of the vitreous tube circumference.

8. A discharge lamp as recited in claim 1, wherein the length of the vitreous tube is approximately 72 inches.

9. A device for effectuating tanning of a person's skin, the device comprising:

a housing structure having a body portion and a base portion, the body portion defining an internal tanning chamber which is adapted and configured for receiving the person;

and a discharge lamp assembly disposed within the internal tanning chamber, the lamp assembly including:

an elongated vitreous tube having an outer periphery and axially opposed first and second ends which define an axial length for the tube therebetween, the outer periphery having a plurality of grooves defined therein and formed along a helical path, wherein the depth of each groove does not exceed 10 percent of the outside diameter of the tube;

a first electrode assembly associated with the first end of the tube;

a second electrode assembly associated with the second end of the tube;

a coating on an interior of the vitreous tube along the entire length for emitting ultraviolet radiation when a voltage is applied across the first and second electrodes, the ultraviolet radiation effectuating the tanning of the person's skin; and a reflective coating on the interior of the vitreous tube and positioned radially inward of the coating, the reflective coating extending about a portion of the vitreous tube circumference.

10. A device as recited in claim 9, wherein the plurality of grooves are interconnected and the helical path is continuous.

11. A device as recited in claim 9, wherein the plurality of grooves are axially offset and the helical path is discontinuous.

12. A device as recited in claim 9, wherein the grooves are formed in the outer periphery of the tube having a pitch of between about 2 inches and about 12 inches.

13. A device as recited in claim 12, wherein the grooves formed in the outer periphery have a depth of between about 0.100 inch to about 0.250 inch.

14. A device as recited in claim 12, wherein the grooves are formed in the outer periphery so as to have a ratio of the groove pitch to the groove depth of about between 8 (in/in) to about 120 (in/in).

15. A device as recited in claim 12, wherein the grooves are formed in the outer periphery so as to have a width of about 0.250 inch to 1.0 inch and a ratio of the groove pitch to the groove width of about between 2 (in/in) to about 48 (in/in).

16. A device as recited in claim 9, wherein the length of the vitreous tube is approximately 72 inches.

17. A discharge lamp for use in tanning applications comprising:

an elongated vitreous tube having an outer periphery and axially opposed first and second ends which define an axial length for the tube therebetween, the outer periphery having a plurality of grooves defined therein and positioned along an axially extending helical path, the tube having an outside diameter of about between 0.25 inch and 2.5 inches and the grooves having a depth of between about 0.100 inch to about 0.250 inch and;

a first electrode assembly associated with the first end of the tube;

a second electrode assembly associated with the second end of the tube;

a coating on an interior of the tube along the entire length for emitting ultraviolet radiation when a voltage is applied across the first and second electrodes; and a reflective coating on the interior of the vitreous tube and positioned radially inward of the coating, the reflective coating extending about a portion of the vitreous tube circumference.

18. A discharge lamp as recited in claim 17, wherein the plurality of grooves are interconnected and the helical path is continuous.

19. A discharge lamp as recited in claim 17, wherein the plurality of grooves are axially offset and the helical path is discontinuous.

20. A discharge lamp as recited in claim 17, wherein the grooves are formed in the outer periphery of the tube having a pitch of between about 2 inches and about 12 inches.

21. A discharge lamp as recited in claim 20, wherein the grooves are formed in the outer periphery so as to have a ratio of the groove pitch to the groove depth of about between 8 (in/in) to about 120 (in/in).

22. A discharge lamp as recited in claim 20, wherein the grooves are formed in the outer periphery so as to have a ratio of the groove pitch to a groove width of about between 2 (in/in) to about 48 (in/in).

23. A method of exposing a person to ultraviolet radiation comprising the steps of:

a) positioning a discharge lamp assembly in proximity to a person, the discharge lamp including:

an elongated vitreous tube having an outer periphery and axially opposed first and second ends which define an axial length for the tube therebetween, the outer periphery having a plurality of grooves defined therein and formed along a helical path, the grooves having a depth of between about 0.100 inch to about 0.250 inch and;

a first electrode assembly associated with the first end of the tube;

a second electrode assembly associated with the second end of the tube;

a coating on an interior of the vitreous tube along the entire length for emitting ultraviolet radiation in tanning wavelengths when a voltage is applied across the first and second electrodes; and a reflective coating on the interior of the vitreous tube and positioned radially inward of the coating, the reflective coating extending about a portion of the vitreous tube circumference.

b) energizing said discharge lamp for a period of time to effect skin tanning of said person.

* * * * *